(12) United States Patent
Milella, Jr. et al.

(10) Patent No.: US 11,602,353 B2
(45) Date of Patent: Mar. 14, 2023

(54) ADJUSTABLE CUTTING GUIDE APPARATUS FOR USE IN ORTHOPEDIC SURGERY

(71) Applicant: ECA MEDICAL INSTRUMENTS, INC., Newbury Park, CA (US)

(72) Inventors: Michael J. Milella, Jr., Newbury Park, CA (US); Lane Hale, Newbury Park, CA (US); E. Marlowe Goble, Newbury Park, CA (US)

(73) Assignee: ECA Medical Instruments, Thousand Oaks, CA (US)

( * ) Notice: Subject to any disclaimer, the term of this patent is extended or adjusted under 35 U.S.C. 154(b) by 81 days.

(21) Appl. No.: 17/075,247

(22) Filed: Oct. 20, 2020

(65) Prior Publication Data
US 2022/0117610 A1    Apr. 21, 2022

(51) Int. Cl.
*A61B 17/15* (2006.01)
*A61B 17/00* (2006.01)

(52) U.S. Cl.
CPC ............ *A61B 17/15* (2013.01); *A61B 17/155* (2013.01); *A61B 2017/0023* (2013.01); *A61B 2017/00477* (2013.01)

(58) Field of Classification Search
CPC ...... A61B 17/15; A61B 17/154; A61B 17/155
See application file for complete search history.

(56) References Cited

U.S. PATENT DOCUMENTS

| | | | | |
|---|---|---|---|---|
| 4,349,018 A | * | 9/1982 | Chambers | A61B 17/152 606/88 |
| 4,926,847 A | | 5/1990 | Luckman | |
| 5,749,876 A | * | 5/1998 | Duvillier | A61B 17/155 606/88 |
| 2006/0293681 A1 | * | 12/2006 | Claypool | A61B 17/155 606/87 |
| 2007/0270872 A1 | | 11/2007 | Thau | |
| 2008/0312659 A1 | * | 12/2008 | Metzger | G16H 20/40 128/898 |
| 2013/0296871 A1 | | 11/2013 | Lazar | |
| 2013/0296872 A1 | | 11/2013 | Davison | |
| 2013/0325017 A1 | * | 12/2013 | Lomicka | A61B 17/15 606/87 |
| 2017/0128079 A1 | * | 5/2017 | Brown | A61B 17/155 |
| 2019/0076154 A1 | | 3/2019 | Herzog | |
| 2019/0274696 A1 | * | 9/2019 | Goble | A61B 17/1764 |

OTHER PUBLICATIONS

International Search Report Issued in PCT/US21/55916; dated Jan. 28, 2022.
International Written Opinion Issued in PCT/US21/55916; dated Jan. 28, 2022.

* cited by examiner

*Primary Examiner* — Larry E Waggle, Jr.
(74) *Attorney, Agent, or Firm* — Ferguson Case Orr Paterson (57) ABSTRACT

Cutting guides for use in orthopedic surgery are disclosed. In some embodiments, the cutting guides comprise monolithic polymer cutting blocks with one or more slots and guide inserts to allow for the provision of various desired surgical cuts to a bone by a cutting saw. In other embodiments, the cutting guides may comprise adjustable guide bars with one or more slots and inserts to allow for various desired surgical cuts to a bone. The location and directionality of the cuts may be configured to match the geometry of a surgical implant.

14 Claims, 6 Drawing Sheets

ADJUSTABLE CUTTING GUIDE APPARATUS FOR USE IN ORTHOPEDIC SURGERY

BACKGROUND OF THE DISCLOSURE

Field of the Disclosure

The present disclosure relates to medical devices, in particular, cutting guides for use in orthopedic surgical procedures, including but not limited to, knee arthroplasty, ankle arthroplasty, wrist arthroplasty, shoulder arthroplasty, and osteotomy.

Description of the Related Art

Knee arthroplasty, or total knee replacement, is a surgical procedure to resurface a knee joint with severe damage. During a knee arthroplasty procedure, a surgeon will resurface a patient's distal femur, proximal tibia, and/or patella so that an artificial knee prosthesis can be fitted to the patient's knee. The femoral component of the prosthesis generally has a smooth outer curvature configured to interface with the tibial component of the prosthesis and a plurality of interior planar surfaces configured to interface with the surgically prepared distal femoral surface. The surgeon will form a plurality of cuts to the patient's distal femur using a surgical cutting instrument, such as a sagittal saw, in order to prepare the distal femur to receive the femoral component of the prosthesis. One concern during the procedure is ensuring the precise location of each of these cuts to the distal femur, so typically the surgeon will use a cutting guide for precision.

Traditional cutting guides known throughout the art are normally made from large metal pieces for stability and sturdiness to minimize the wear and tear caused by recurrent surgical procedures. For example, U.S. Pat. No. 8,052,692 discloses a cutting guide for use in knee arthroplasty, touting the cutting guide's stability and structural continuity provided by "more mass of material" and criticizing other designs with less metal as less stable and more likely to break during operation.

Although a metallic cutting guide may have been an attractive option for stability reasons, it increases the cost of manufacturing the cutting guide and necessitates its reuse for numerous procedures over a long period of time. The high expense is disadvantageous because it limits the number of cutting guides available in house to surgeons. Additionally, a reusable cutting guide must be sterilized before each use, which can take up to 5-6 hours, and must be recalibrated periodically, which further affects the time and cost associated with maintaining a reusable cutting guide. Therefore, in hospitals and offices that are only able to afford to keep one cutting guide in house, a surgeon will have to wait to perform subsequent procedures until the cutting guide has been sterilized and/or recalibrated, greatly limiting the number of procedures that can be performed in one day. In contrast, a cost-effective, single use cutting guide requires no sterilization process or recalibration because it will be disposed of after each use, presenting virtually no limitations on how many procedures a surgeon could perform in a single day.

Thus, there is a need for a single use cutting guide with a low enough cost of manufacturing as to justify disposing of the cutting guide after a single procedure and purchasing a new cutting guide for each subsequent procedure. The single use cutting guide must also be sufficiently durable and reliable to allow the surgeon to perform a successful procedure. The present disclosure includes such a device that is lower in cost than traditional cutting guides but remains sufficiently reliable for successful procedures.

SUMMARY OF THE DISCLOSURE

The present disclosure includes single use cutting guides to be used in various orthopedic surgical procedures such as knee arthroplasty, ankle arthroplasty, and wrist arthroplasty. In some embodiments, the cutting guide comprises a polymer substrate cutting block and metal guide inserts that are insert molded into the cutting block. It is understood that other assembly methods for the cutting guide are possible such as press-fitting the metal guide inserts into the polymer substrate cutting block, for example. In other embodiments, the cutting guide comprises a plurality of polymer guide bars mounted on a polymer base and metal guide inserts that are insert molded into the guide bars. In certain embodiments, the cutting guide further comprises pins to secure the guide to a patient's bone during a procedure. These and other elements of the present disclosure allow for a cost-effective yet reliable cutting guide that can be successfully used for a single procedure and then discarded.

These and other further features and advantages provided in this disclosure would be apparent to those skilled in the art from the following detailed description, taken together with the accompanying drawings.

DETAILED DESCRIPTION OF THE DISCLOSURE

Throughout this disclosure, the embodiments illustrated should be considered as exemplars, rather than as limitations on the present disclosure. As used herein, the term "invention," "device," "apparatus," "method," "disclosure," "present invention," "present device," "present apparatus," "present method," or "present disclosure" refers to any one of the embodiments of the disclosure described herein, and any equivalents. Furthermore, reference to various features of the "invention," "device," "apparatus," "method," "disclosure," "present invention," "present device," "present apparatus," "present method," or "present disclosure" throughout this document does not mean that all claimed embodiments or methods must include the reference features.

It is also understood that when an element or feature is referred to as being "on" or "adjacent" to another element or feature, it can be directly on or adjacent the other element or feature or intervening elements or features may also be present. In contrast, when an element is referred to as being "directly on" or extending "directly onto" another element, there are no intervening elements present. Additionally, it is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Furthermore, relative terms such as "inner," "outer," "upper," "top," "above," "lower," "bottom," "beneath," "below," and similar terms, may be used herein to describe a relationship of one element to another. Terms such as "higher," "lower," "wider," "narrower," and similar terms, may be used herein to describe angular relationships. It is understood that these terms are intended to encompass different orientations of the elements or system in addition to the orientation depicted in the figures.

Although the terms first, second, third, etc., may be used herein to describe various elements, components, regions, and/or sections, these elements, components, regions, and/or sections should not be limited by these terms. These terms are only used to distinguish one element, component, region, or section from another. Thus, unless expressly stated otherwise, a first element, component, region, or section discussed below could be termed a second element, component, region, or section without departing from the teachings of the present disclosure. As used herein, the term "and/or" includes any and all combinations of one or more of the associated list items.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. For example, when the present specification refers to "an" assembly, it is understood that this language encompasses a single assembly or a plurality or array of assemblies. It is further understood that the terms "comprises," "comprising," "includes," and/or "including" when used herein, specify the presence of stated features, integers, steps, operations, elements, and/or components, but do not preclude the presence or addition of one or more other features, integers, steps, operations, elements, components, and/or groups thereof.

Embodiments as described in the present disclosure can be described herein with reference to view illustrations, some of which are schematic in nature. As such, the actual thickness of elements can be different, and variations from the shapes of the some of the illustrations as a result, for example, of manufacturing techniques and/or tolerances are expected. Thus, the elements illustrated in the some of the figures are schematic in nature and their shapes are not intended to illustrate the precise shape of a region and are not intended to limit the scope of the disclosure.

FIGS. 1-4 show one embodiment according to the present disclosure of an orthopedic cutting guide apparatus 100 comprising a cutting block 102. As shown, cutting block 102 may be a monolithic piece that can be made from a variety of materials including, without limitation, polymers, plastics, metals, and/or combinations thereof, with an exemplary material being a polymer substrate. A monolithic polymeric cutting block 102 can provide certain advantages over traditional metal surgical instruments, for example, allowing cutting guide apparatus 100 to be lower cost, more sterile, single-use, and more precise. For example, a polymeric cutting block may be discarded after a single use, which obviates the need for a sterilization process generally required for multi-use devices and reduces the degradation effects of multiple uses. As shown, cutting block 102 comprises opposing proximal and distal surfaces 302, 304, where proximal surface 302 is configured to engage with the distal end of a femur 104 and distal surface 304 is configured to engage with a cutting instrument. Although the present disclosure and figures focus on application of cutting guide apparatus 100 to a femur for use during knee arthroplasty, it is understood that other embodiments of the present disclosure may apply to other medical procedures and parts of the body such as foot and ankle and/or hand and wrist.

As shown, cutting block 102 further comprises opposing anterior and posterior surfaces 202, 204 that correspond to the anterior and posterior sides of femur 104 and are substantially orthogonal with proximal and distal surfaces 302, 304. Further, cutting block 102 may comprise opposing medial and lateral surfaces 206, 208 that correspond to the medial and lateral sides of femur 104, are adjacent to anterior and posterior surfaces 202, 204, and are substantially orthogonal with proximal and distal surfaces 302, 304. As shown in FIGS. 1-4, femur 104 is a left femur, so the terms "medial" and "lateral" are made in reference to a left femur. The selection of the terms "medial" and "lateral" as referring to a left femur is made for convenience purposes only, and it is understood that cutting block 102 may be used to prepare a right femur as well, such that the "medial" side of cutting block 102, as referenced herein, would align with the lateral side of the right femur, and the "lateral" side of the cutting block would align with the medial side of the right femur.

Figure 1:
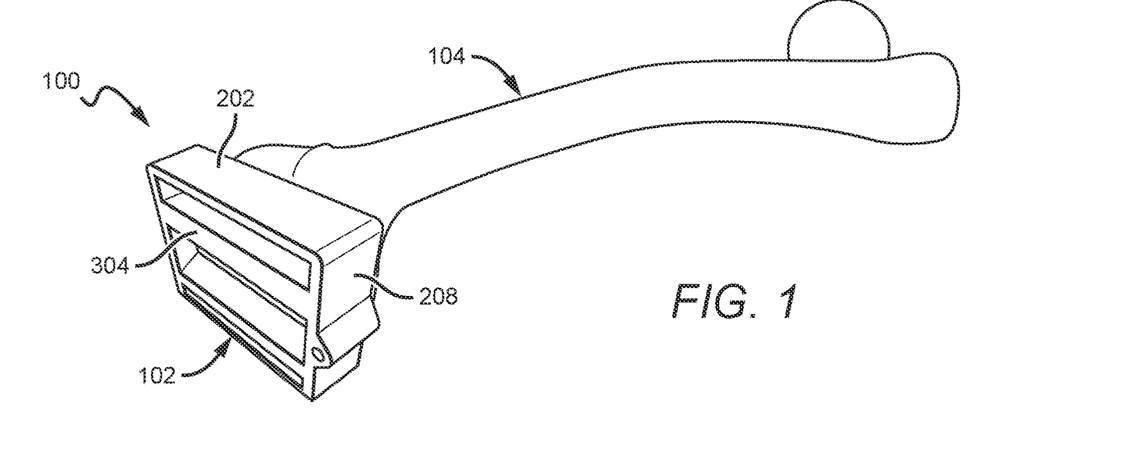
FIG. 1 is a perspective view of a cutting block according to one embodiment of the present disclosure.
Figure 2:
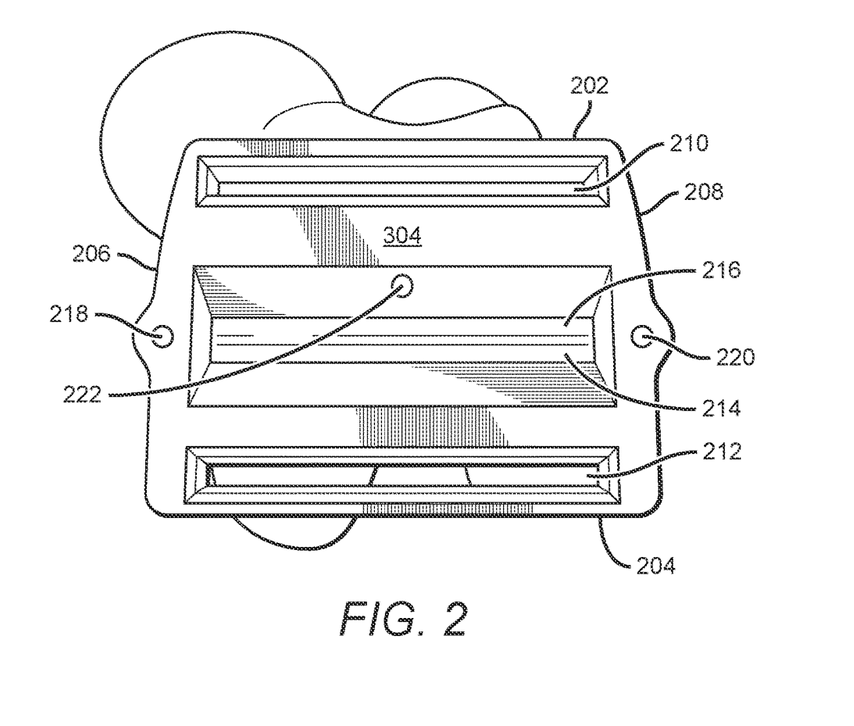
FIG. 2 is a distal end view of a cutting block according to one embodiment of the present disclosure.
Figure 3:
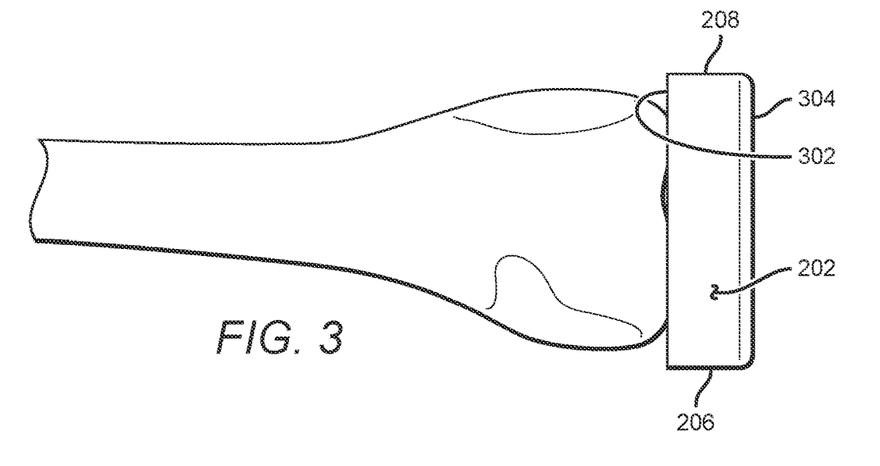
FIG. 3 is an anterior top view of a cutting block according to one embodiment of the present disclosure.
Figure 4:
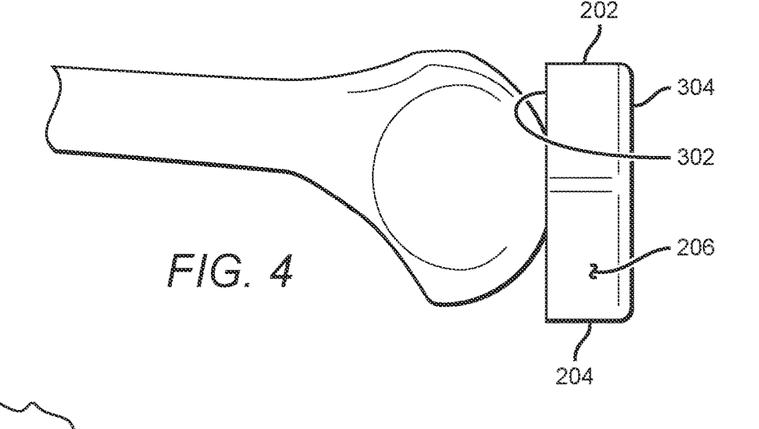
FIG. 4 is a lateral side view of a cutting block according to one embodiment of the present disclosure.

FIG. 2 shows cutting block 102 further comprising first and second slots 210, 212 that traverse substantially orthogonally through proximal and distal surfaces 302, 304, with first slot 210 positioned in an anterior portion of cutting block 102 and second slot 212 in a posterior portion of cutting block 102. Additionally, FIG. 2 shows cutting block 102 comprising third and fourth slots 214, 216 positioned between first and second slots 210, 212 and traversing diagonally through proximal and distal surfaces 302, 304. As shown, third and fourth slots 214, 216 may intersect between proximal and distal surfaces 302, 304. In certain embodiments, first, second, third, and fourth slots 210, 212, 214, 216 may horizontally extend substantially the entire width between medial and lateral surfaces 206, 208. As used herein, the term "horizontal" is defined with reference to the medial/lateral direction of cutting guide apparatus 100 when secured to the distal end of femur 104.

FIG. 2 also shows cutting block 102 comprising first, second, and third pinholes 218, 220, 222 that traverse through proximal and distal surfaces 302, 304, where first pinhole 218 is closest to medial surface 206, second pinhole 220 is closest to lateral surface 208, and third pinhole 222 is between—and in some embodiments centered between—first pinhole 218 and second pinhole 220. In certain embodiments, first, second, and third pinholes 218, 220, 222 may traverse through proximal and distal surfaces 302, 304 substantially orthogonally, while in other embodiments, first, second, and third pinholes 218, 220, 222 may traverse through proximal and distal surfaces 302, 304 at an oblique angle. Although the embodiment shown in FIG. 2 has three pinholes, it is understood that other embodiments may comprise different numbers of pinholes such as two pinholes, four pinholes, five pinholes, or any other reasonable number of pinholes.

Figure 5:
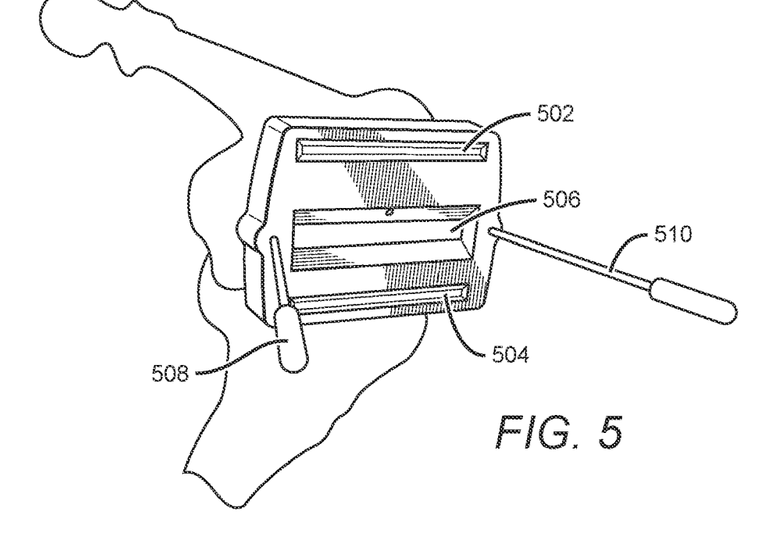
FIG. 5 is a perspective view of a cutting guide apparatus comprising a cutting block, guide inserts, and pins according to one embodiment of the present disclosure.

As shown in FIG. 5, cutting guide apparatus 100 may further comprise first, second, and third guide inserts 502, 504, 506, where first guide insert 502 is positioned within first slot 210, second guide insert 504 is positioned within second slot 212, and third guide insert 506 is positioned within third and fourth slots 214, 216 nearer distal surface 304 than proximal surface 302. First, second, and third guide inserts 502, 504, 506 can be made from a variety of materials including, without limitation, polymers, plastics, metals, and/or combinations thereof, with an exemplary material being a metal or metal alloy (e.g., steel) to interact with surgical cutting instruments such as a sagittal saw. Further, first, second, and third guide inserts 502, 504, 506 may be insert molded to be fixed within their respective first, second, third, and/or fourth slot 210, 212, 214, 216. First, second, and third guide inserts 502, 504, 506 may be produced in a variety of ways, for example, 3D printed or fabricated from sheet-metal. Although the embodiment shown in FIG. 5 has three guide inserts, it is understood that other embodiments may comprise different numbers of slots and guide inserts. For example, an alternative embodiment not shown may comprise one slot and guide insert in the center of cutting guide 100 where guide insert 506 is shown in FIG. 5. Any number of desired slots and guide inserts may be used.

FIG. 5 also shows a plurality of pins that are configured to pass through first, second, and/or third pinholes 218, 220, 222 and secure cutting guide apparatus 100 to the distal end of femur 104. Although FIG. 5 only shows two pins 508, 510 passing through first and second pinholes 218, 220, it is understood that other embodiments may comprise additional pins, for example, a third pin configured to pass through third pinhole 222. The plurality of pins can be made from a variety of materials including, without limitation, polymers, plastics, metals, and/or combinations thereof, with an exemplary material being a metal or metal alloy (e.g., steel) to ensure a secure connection between cutting guide apparatus 100 and the distal end of femur 104.

In certain embodiments, the only metal parts of cutting guide apparatus 100 are the guide inserts and pins, which allows cutting guide apparatus 100 to be discarded or recycled after a single use, offering benefits over traditional cutting guides such as providing a more cost-effective, precise, and sterile surgical procedure. Embodiments of the present disclosure are more cost-effective because a non-metal cutting block 102 significantly reduces the materials cost of producing cutting guide apparatus 100, where metal parts are generally more costly than non-metal parts, and reducing the amount of metal therefore reduces the overall cost of the cutting guide apparatus. Additionally, embodiments of the present disclosure are more precise because they can be discarded after a single use, which means that they are not susceptible to the wear and tear of recurring procedures, nor do they inflict as much damage to the surgical cutting instrument or need to be recalibrated after each procedure. Further, embodiments of the present disclosure are more sterile because they are only used for one patient, reducing the chance of contamination from prior procedures. Traditional cutting guides need to be sterilized after each use, which not only increases the risk of contamination, but also requires time (up to 5-6 hours) and other resources to be expended on the sterilization process. This may further reduce the number of procedures that a single hospital or practice can perform in a day where the number of available cutting guides are limited (in some instances, to only one due to the high cost of metal cutting guides) and a physician needs to wait until the cutting guides are sterilized before performing subsequent procedures.

Figure 6:
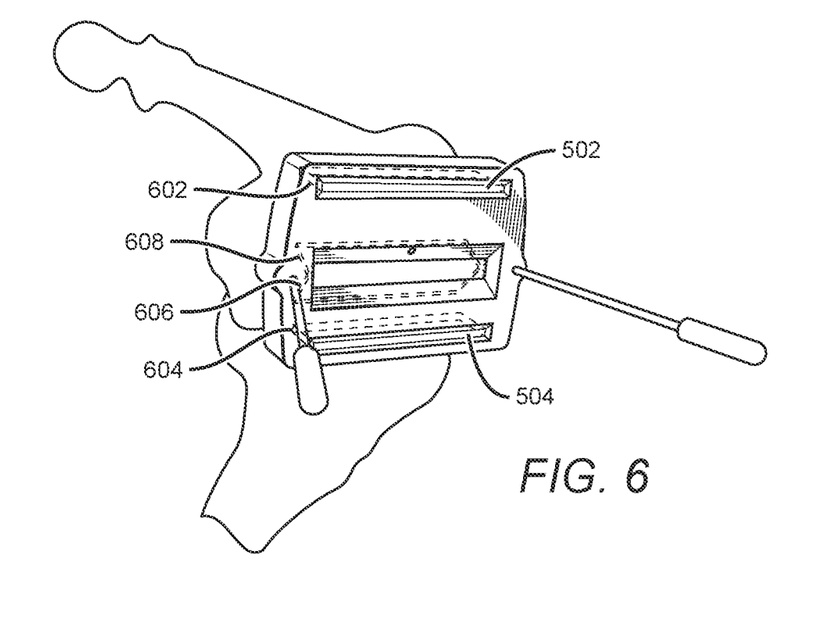
FIG. 6 is a perspective view of the embodiment shown in FIG. 5 with the internal configuration of the guide inserts shown in broken line.

Referring now to FIG. 6, first guide insert 502 comprises a first slit 602, second guide insert 504 comprises a second slit 604, and third guide insert comprises third and fourth slits 606, 608. FIG. 6 shows, in broken line, the interior configuration and location of first, second, third, and fourth slits 602, 604, 606, 608. These slits can be sized to sufficiently accommodate a surgical cutting instrument such as a sagittal saw and formed to provide desired angles and locations for the cuts. In certain embodiments, different guide inserts could be insert molded into the same cutting block such that one cutting block 102 could support numerous different cutting configurations. This is advantageous over traditional cutting guides that do not have guide inserts molded into a cutting block because it allows for one universal cutting block to be versatile and adaptable to different surgical systems and procedures.

Figure 7:
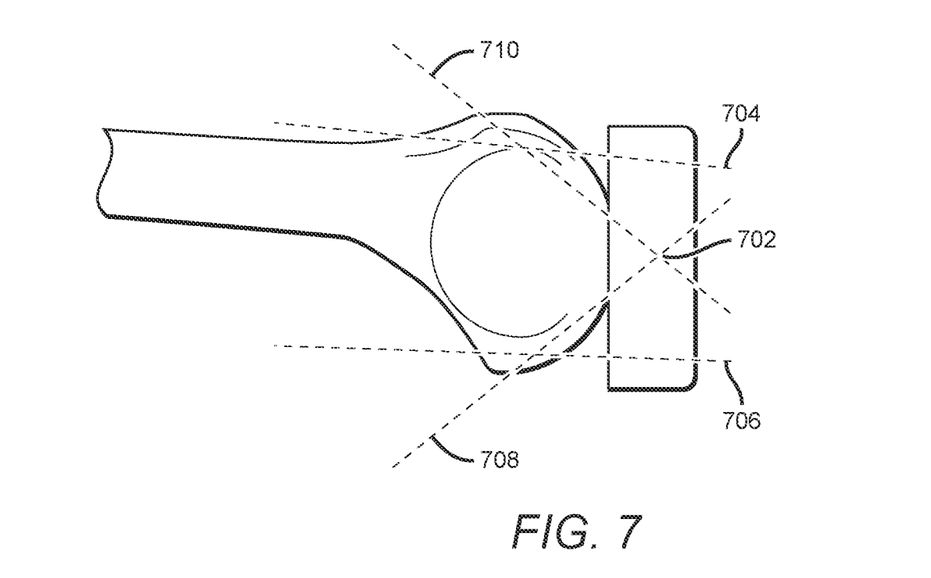
FIG. 7 is a lateral side view of a cutting guide apparatus according to one embodiment of the present disclosure with cut paths shown in broken line.

FIG. 7 shows, in broken line, the direction of various cuts made to femur 104 through first, second, third, and fourth slits 602, 604, 606, 608. As shown, first slit 602 is configured to allow for a planar anterior cut 704 (i.e., a cut configured to closely match the geometry of an implant and generally made substantially perpendicular to the anterior surface plane of the anterior portion of cutting guide apparatus 100) on the distal end of femur 104 by a surgical cutting instrument. Second slit 604 is configured to allow for a planar posterior cut 706 (i.e., a cut configured to closely match the geometry of an implant and generally made substantially perpendicular to the posterior surface plane of the posterior portion of cutting guide apparatus 100) on the distal end of femur 104 by a surgical cutting instrument. A person of skill in the art would understand that while cuts may be intended to be perpendicular or at another specified angle, in practice, these cuts may vary acceptably from these angles given a particular tolerance level. Third slit 606 is configured to allow for a chamfered posterior cut 708 on the distal end of femur 104 by a surgical cutting instrument. Fourth slit 608 is configured to allow for a chamfered anterior cut 710 on the distal end of femur 104 by a surgical cutting instrument. FIG. 7 also shows that third and fourth slots 214, 216 may intersect along a midline 702 between anterior surface 202 and posterior surface 204.

Figure 8:
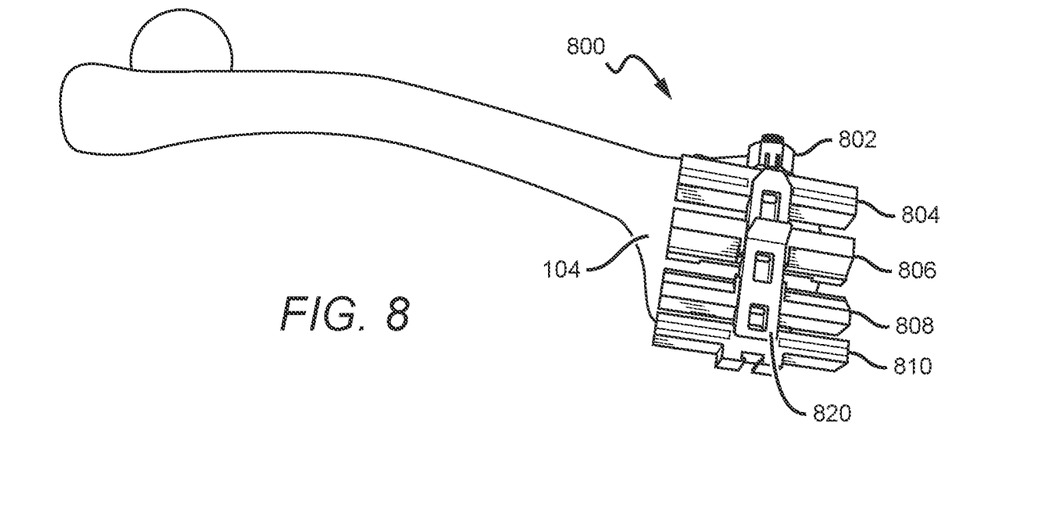
FIG. 8 is a perspective view of an adjustable cutting guide apparatus according to one embodiment of the present disclosure.
Figure 9:
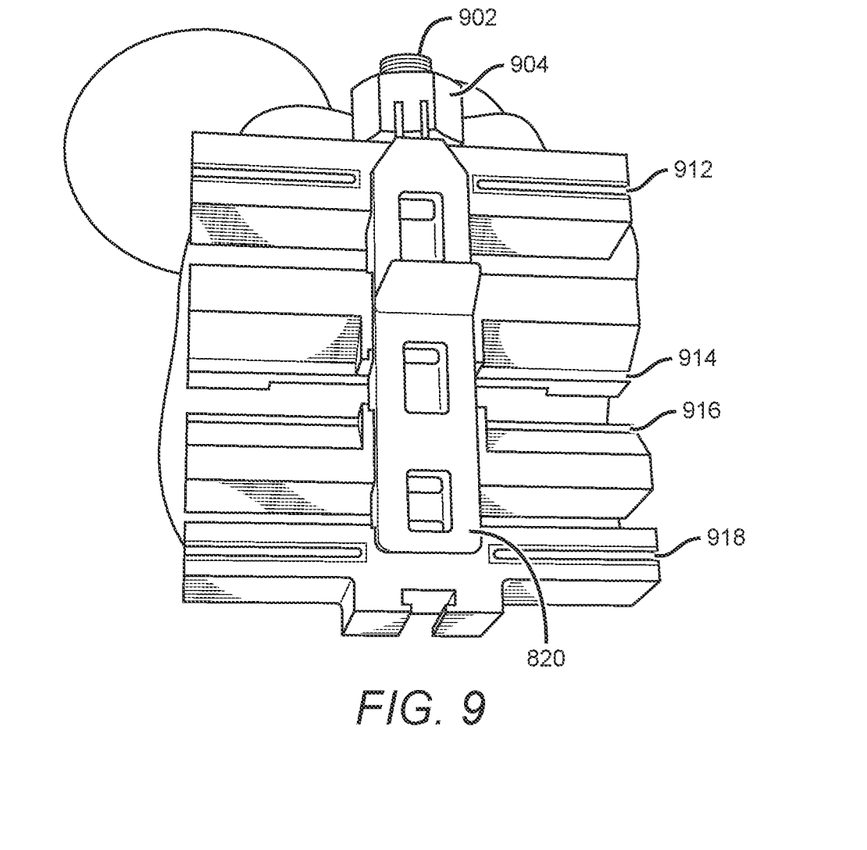
FIG. 9 is a distal/end view of an adjustable cutting guide apparatus according to one embodiment of the present disclosure.
Figure 10:
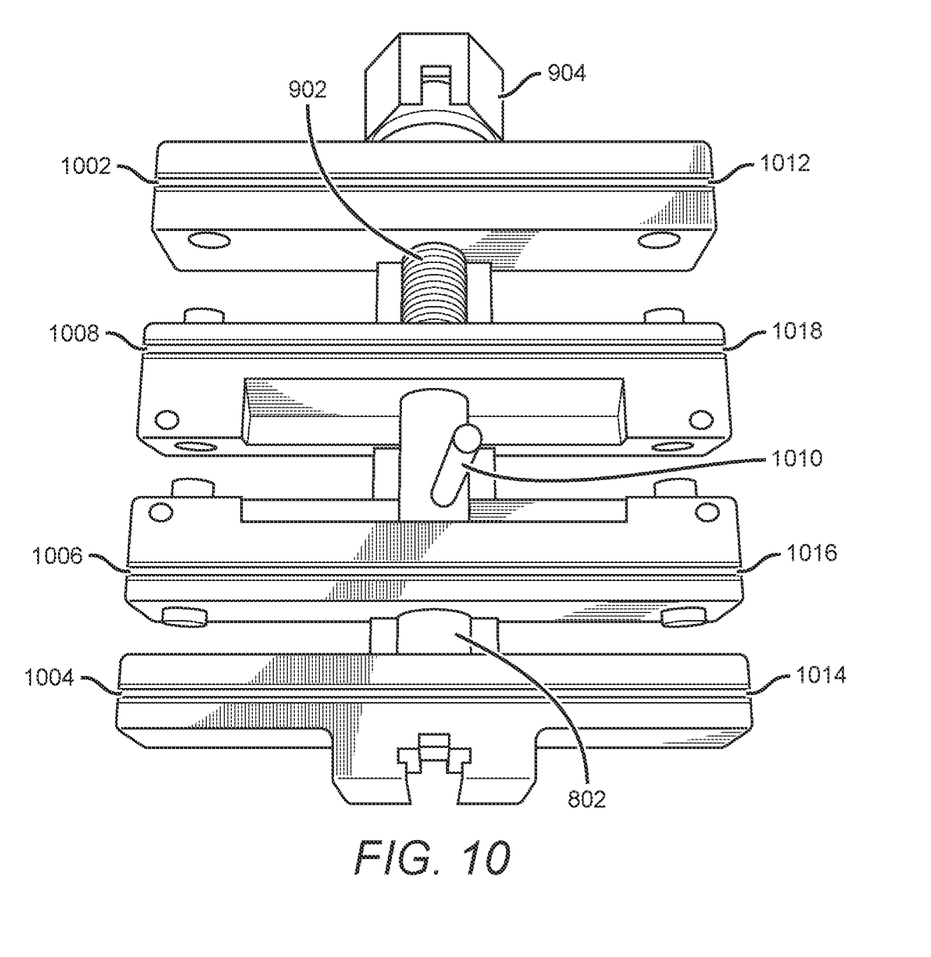
FIG. 10 is a proximal view of an adjustable cutting guide apparatus according to one embodiment of the present disclosure.

FIGS. 8-10 show another embodiment of a cutting guide 800 according to the present disclosure comprising a plurality of adjustable guide bars 804, 806, 808, 810 mounted on a base 802. Guide bars 804, 806, 808, 810 and base 802 may be made from a variety of materials such as a polymer (e.g., plastics) or metal (e.g., steel), with one suitable material being polymer. Each guide bar may comprise at least one slot 912, 914, 916, 918. In the embodiment shown in FIG. 9, each guide bar comprises two slots, one on either side of base 802. A plurality of guide inserts 1002, 1004, 1006, 1008 may be positioned within each slot 912, 914, 916, 918. Guide inserts 1002, 1004, 1006, 1008 may be made from a variety of materials, with one suitable material being metal, and may also be insert molded or press-fit into slots 912, 914, 916, 918.

Figure 11:
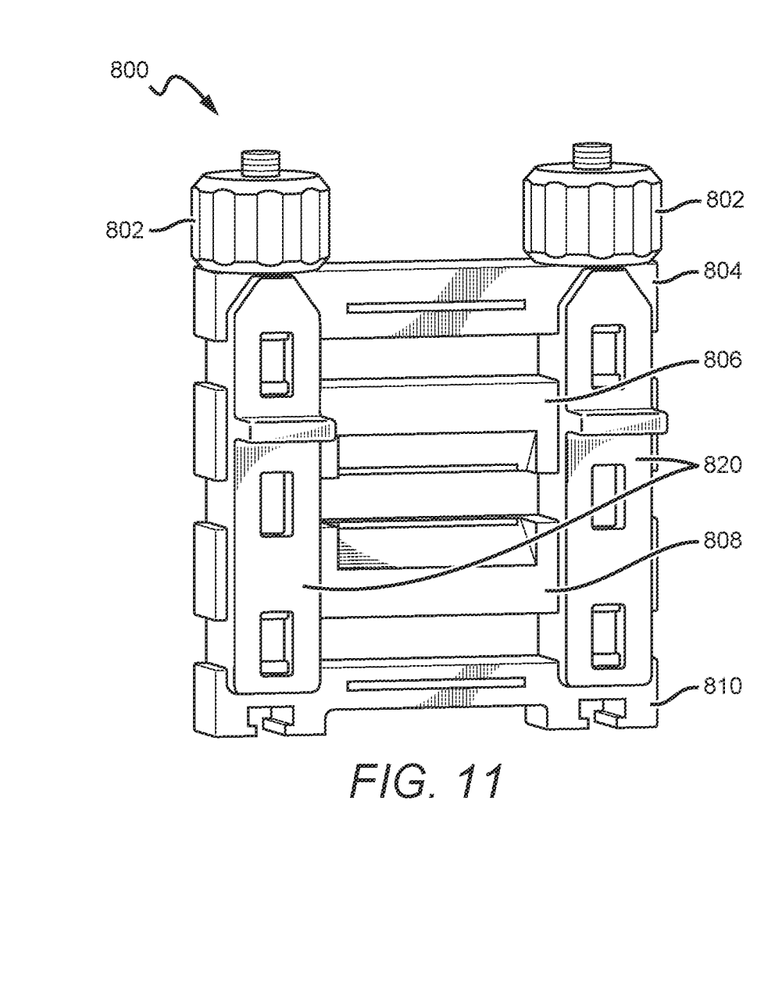
FIG. 11 is a perspective view of a cutting guide apparatus according to one embodiment of the present disclosure.
Figure 12:
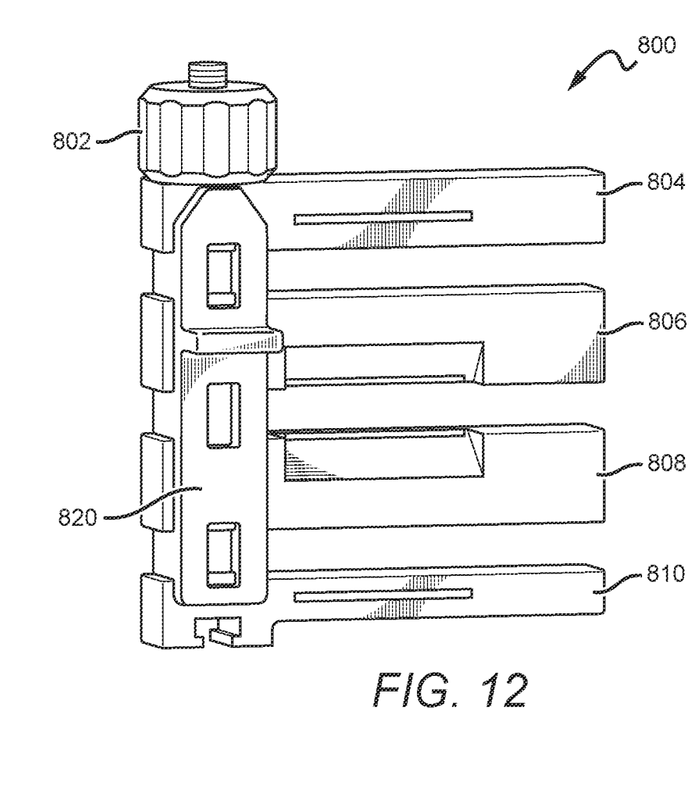
FIG. 12 is a perspective view of a cutting guide apparatus according to one embodiment of the present disclosure.

A guide key 820 may be applied to guide bars 804, 806, 808, 810 to fix the guide bars in place along base 820. Without guide key 820, guide bars 804, 806, 808, 810 can slide along base 820, which allows for adjustability of the guide bars until they are locked into place by guide key 820. Guide key 820 maintains the spatial relationship between guide bars 804, 806, 808, 810 along base 802. Different guide keys 820 can be interchanged and can allow for different spacing between guide bars 804, 806, 808, 810 such that cutting guide 800 can be applied to various sizes and types of bones. In some embodiments, guide bars 804, 806, 808, 810 may engage with each other. Base 802 may comprise a screw thread 902 at one end or throughout to allow a cap 904 to attach at the top of base 802 above the top guide bar 804, which in connection with guide key 820, further locks guide bars 804, 806, 808, 810 in place. Although base 802, guide key 820, screw thread 902, and cap 904 are shown in the center of cutting guide 800, it is understood that other locations are possible, such as at the medial or lateral end of cutting guide 800 or at any other reasonable location along cutting guide 800. In some embodiments, base 802, guide key 820, screw thread 902, and cap 904 may be replaced with two of each element that are positioned at the medial and lateral outer edges of guide bars 804, 806, 808, 810. Examples of these different embodiments are shown in FIGS. 11 and 12.

As with the embodiments discussed above, the cutting guide 800 can be applied to a bone, such as the distal end of femur 104, for use in orthopedic surgery (e.g., knee arthroplasty, ankle arthroplasty, and wrist arthroplasty). A first of said guide inserts 1002 may comprise a first slit 1012 configured to allow for a planar anterior cut to bone 104. A second of said guide inserts 1004 may comprise a second slit 1014 configured to allow for a planar posterior cut to bone 104. A third of said guide inserts 1006 may comprise a third slit 1014 configured to allow for a chamfered posterior cut to bone 104. A fourth of said guide inserts 1008 may comprise a fourth slit 1018 configured to allow for a chamfered anterior cut to bone 104. Additionally, one or more pins 1010 may pass through base 802 via one or more pinholes at various angles for securing cutting guide 800 to bone 104.

It is understood that embodiments presented herein are meant to be exemplary. Embodiments of the present disclosure can comprise any combination or compatible features shown in the various figures, and these embodiments should not be limited to those expressly illustrated and discussed.

Although the present disclosure has been described in detail with reference to certain configurations thereof, other versions are possible. Therefore, the spirit and scope of the disclosure should not be limited to the versions described above. The foregoing is intended to cover all modifications and alternative constructions falling within the spirit and scope of the disclosure as expressed in the appended claims, wherein no portion of the disclosure is intended, expressly or implicitly, to be dedicated to the public domain if not set forth in the claims.

What is claimed is:

1. An orthopedic cutting guide apparatus, comprising:
    a base wherein a first end of said base comprises a screw thread;
    a cap configured to screw into said screw thread;
    a plurality of polymeric guide bars mounted on said base, wherein each of said guide bars comprises at least one slot;
    a plurality of guide inserts positioned within each of said slots; and
    a guide key configured to fix each of said guide bars along said base such that said guide bars maintain a fixed spatial relationship when said guide key is engaged.

2. The cutting guide apparatus of claim 1, wherein said guide bars are configured to slide along said base when said guide key is disengaged.

3. The cutting guide apparatus of claim 1, wherein a first of said guide inserts comprises a first slit configured to allow for a planar anterior cut to a distal end of a bone.

4. The cutting guide apparatus of claim 1, wherein a second of said guide inserts comprises a second slit configured to allow for a planar posterior cut to a distal end of a bone.

5. The cutting guide apparatus of claim 1, wherein a third of said guide inserts comprises a third slit configured to allow for a chamfered posterior cut to a distal end of a bone.

6. The cutting guide apparatus of claim 1, wherein a fourth of said guide inserts comprises a fourth slit configured to allow for a chamfered anterior cut to a distal end of a bone.

7. The cutting guide apparatus of claim 1, further comprising a pin passing through said base via a pinhole and configured to secure said cutting guide apparatus to a bone.

8. The cutting guide apparatus of claim 1, wherein said base and guide key are positioned in a center of said cutting guide apparatus.

9. The cutting guide apparatus of claim 1, wherein said plurality of guide bars are configured to engage with each other.

10. An orthopedic cutting guide apparatus, comprising:
    a plurality of polymeric guide bars, wherein each of said guide bars comprises at least one slot;
    a plurality of guide inserts positioned within each of said slots;
    a first base positioned along a medial edge of said plurality of guide bars;
    a second base positioned along a lateral edge of said plurality of guide bars;
    a first guide key configured to fix each of said guide bars along said first base;
    a second guide key configured to fix each of said guide bars along said second base,
    wherein said guide bars maintain a fixed spatial relationship when said guide key is engaged.

11. The cutting guide apparatus of claim 10, wherein a first end of said first base comprises a first screw thread and a first end of said second base comprises a second screw thread.

12. The cutting guide apparatus of claim 11, further comprising a first cap configured to screw into said first screw thread and a second cap configured to screw into said second screw thread.

13. The cutting guide apparatus of claim 10, wherein said guide bars are configured to slide along said first and second bases when said first and second guide keys are disengaged.

14. The cutting guide apparatus of claim 10, further comprising one or more pins passing through said first and/or second bases via one or more pinholes and configured to secure said cutting guide apparatus to a bone.

* * * * *